United States Patent [19]

Corkins

[11] 4,264,528

[45] Apr. 28, 1981

[54] METHOD OF PREPARING KETOXIME CARBAMATES

[75] Inventor: H. Glenn Corkins, Mentor, Ohio

[73] Assignee: Diamond Shamrock Corporation, Dallas, Tex.

[21] Appl. No.: 160,912

[22] Filed: Jun. 18, 1980

Related U.S. Application Data

[63] Continuation of Ser. No. 966,388, Dec. 4, 1978, abandoned.

[51] Int. Cl.³ .............................................. C07C 131/00
[52] U.S. Cl. .................................. 564/253; 564/255; 564/268
[58] Field of Search ..................... 260/566 AC, 566 A

[56] References Cited

U.S. PATENT DOCUMENTS

| | | | |
|---|---|---|---|
| 3,658,869 | 4/1972 | Soloway et al. ................. | 260/566 A |
| 3,752,841 | 8/1973 | Fuchs ............................. | 260/566 AC |
| 3,875,232 | 4/1975 | Magee ........................... | 260/566 AC |

OTHER PUBLICATIONS

Wagner, Romeo R. et al., "Synthetic Organic Chemistry", (1968), p. 9, Wiley & Sons, Publ.

*Primary Examiner*—Jane S. Myers
*Assistant Examiner*—L. Hendriksen
*Attorney, Agent, or Firm*—John J. Freer

[57] ABSTRACT

A novel process of preparing ketoxime carbamate by forming a halogenated intermediate which is reacted with an alkali metal compound and an isocyanate.

8 Claims, No Drawings

METHOD OF PREPARING KETOXIME CARBAMATES

This is a continuation of application Ser. No. 966,388, filed Dec. 4, 1978, now abandoned.

BACKGROUND OF THE INVENTION

The present invention relates to the synthesis of organic compounds, and, more particularly, to the synthesis of certain ketoxime carbamates.

U.S. Pat. No. 3,875,232 and a number of subsequent related United States patents have issued to Thomas A. Magee disclosing and claiming certain novel ketoxime carbamate compositions. These compositions are described by the formula:

$$\begin{array}{c} R_1 \\ | \\ R_2-C_3-C_2 \\ | \\ R_3 \end{array} \begin{array}{c} O \quad R_6 \\ \| \quad / \\ N-OCN \\ \| \quad \backslash \\ \quad\quad R_7 \\ \quad\quad | \\ \quad\quad C_1-X \\ \quad\quad | \\ \quad\quad Y \end{array}$$

where
$R_1$ = hydrogen, $R_2$-$R_3$ or X;
$R_2$-$R_3$ = lower alkyl, lower alkenyl, lower alkynyl, substituted lower alkyl, alkenyl, or alkynyl with the proviso that $R_2$ and $R_3$ may be connected to form a cycloaliphatic ring;
$R_6$-$R_7$ = hydrogen, lower alkyl, lower alkenyl, or lower alkynyl;
Y = H or X;
X = is selected from the group consisting of $SR_8$, $S(O)R_8$, $SO_2R_8$, $OR_8$, $OSO_2R_8$, $NR_8R_9$, $NO_2$, CN, SCN, $N_3$, or halogen with the proviso that when X and Y are $OR_8$, $SR_8$ $S(O)R_8$, $SO_2R_8$, or $NR_8R_9$, X and Y may be connected to form a heterocyclic ring;
$R_8$ = hydrogen, lower alkyl, lower alkenyl, lower alkynyl, aryl, substituted aryl, carbamyl, substituted carbamyl, acyl, or substituted acyl with the proviso that the lower alkyl or alkenyl groups may be further substituted with X; and
$R_9$ = hydrogen or lower alkyl with the proviso that $R_8$, $R_9$ and N in the $NR_8R_9$ group may form a heterocyclic ring.

The term lower alkyl radical means a radical having from one to about seven carbon atoms.

According to Magee, the compounds can be prepared by one of three basic methods. The first method (referred to by Magee as Method A) involves reaction of an isocyanate with an oxime as shown, for example, in the equation:

$$\begin{array}{c} R_1 \; NOH \; H \\ | \quad \| \quad | \\ R_2-C-C-\!\!\!-\!\!\!-\!\!\!-C-X + R_6NCO \longrightarrow \\ | \quad\quad\quad\quad | \\ R_3 \quad\quad\quad\; Y \end{array}$$

$$\begin{array}{c} \quad\quad O \quad H \\ \quad\quad \| \quad / \\ \quad\quad NOCN \\ R_1 \quad\quad \backslash \; H \\ | \quad\quad\quad R_6 \; | \\ R_2-C-C-\!\!\!-\!\!\!-\!\!\!-C-X \\ | \quad\quad\quad\quad\;\; | \\ R_3 \quad\quad\quad\quad Y \end{array}$$

wherein $R_1$ through $R_6$ and X are defined above. The oxime and isocyanate are reacted in an inert organic solvent from about 0° C. to about 150° C., preferably from about 20° C. to about 80° C., and at a pressure from about 1 to 10 atmospheres, preferably from about 1 to about 3 atmospheres. Reaction pressure is determined by reaction temperature, concentration and vapor pressure of the isocyanate. Preferably, reaction is carried out in the presence of from about 0.1 to about 1.0 percent, by weight, based on the weight of reactants, of a tertiary amine catalyst such as triethyl amine, N,N-dimethylaniline, or the like. The molar ratio of isocyanate to oxime can vary from about 0.1:1 to about 10:1. An equimolar amount or slight excess of isocyanate is preferred to ensure complete reaction of the oxime. Reaction times can vary from a few minutes to several days. Usually, reaction times of from about one-half to about six hours are sufficient.

A second method (referred to by Magee as Method B) involves reaction of an oxime with phosgene to obtain an oxime chloroformate which is then reacted with an amine. This method is illustrated in Equations (1) and (2) below:

$$\begin{array}{c} R_1 \; NOH \; H \\ | \quad \| \quad | \\ R_2-C-C-\!\!\!-\!\!\!-\!\!\!-C-X + COCl_2 \longrightarrow \\ | \quad\quad\quad\quad | \\ R_3 \quad\quad\quad\; Y \end{array} \quad (1)$$

$$\begin{array}{c} \quad\quad\quad\quad\quad O \\ \quad\quad\quad\quad\quad \| \\ R_1 \; NOCCl \; H \\ | \quad \| \quad\quad | \\ R_2-C-C-\!\!\!-\!\!\!-\!\!\!-C-X \\ | \quad\quad\quad\quad | \\ R_3 \quad\quad\quad\; Y \end{array}$$

$$\begin{array}{c} \quad\quad\quad\quad O \\ \quad\quad\quad\quad \| \\ R_1 \; NOCCl \; H \quad\quad R_6 \\ | \quad \| \quad\quad | \quad\quad\quad / \\ R_2-C-C-\!\!\!-\!\!\!-\!\!\!-C-X + HN \longrightarrow \\ | \quad\quad\quad\quad | \quad\quad\quad \backslash \\ R_3 \quad\quad\quad\; Y \quad\quad\quad R_7 \end{array} \quad (2)$$

$$\begin{array}{c} \quad\quad\quad\quad O \quad R_6 \\ \quad\quad\quad\quad \| \quad / \\ \quad\quad\quad NOCN \\ R_1 \quad\quad\quad \backslash \; H \\ | \quad\quad\quad\quad R_7 \; | \\ R_2-C-C-\!\!\!-\!\!\!-\!\!\!-C\; X \\ | \quad\quad\quad\quad\;\; | \\ R_3 \quad\quad\quad\quad Y \end{array}$$

In the reaction shown in Equation (1), a solution of the oxime dissolved in an inert solvent as diethyl ether, is added slowly to a solution of phosgene dissolved in an inert solvent in the presence of an HCl acceptor such as a tertiary amine, e.g., N,N-dimethylaniline. Reaction is carried out from about −30° C. to about 100° C., preferably at from about 0° C. to about 50° C. The resulting reaction mixture, a solution of the chloroformate in an inert organic solvent, can be filtered or washed with water to remove amine hydrochloride before it is used in the reaction shown in Equation (2).

In the reaction shown in Equation (2), an amine is added to the chloroformate solution in the presence of an amine solvent such as water, at temperatures between about −40° C. and about 80° C., preferably at about 0° C. to about 40° C. A larger than molar excess of amine can be used so that the amine acts both as reactant and as HCl acceptor and complete conversion of chloroformate is obtained. Alternatively, a separate HCl acceptor, such as tertiary amine, can be used.

The third method (referred to by Magee as Method C) for the preparation of such compositions comprises reacting:

(a) a compound of the formula $$\underset{R_3}{\overset{R_1}{\underset{|}{R_2-C-C}}}\overset{O}{\underset{\|}{\overset{N-OCN}{\|}}}\overset{R_6}{\underset{R_7}{\diagdown}}\overset{H}{\underset{|}{C-Z}}$$

wherein Z is a reactive halogen, and (b) HX, in the presence of an HZ acceptor. This includes reaction of the haloketones with mercaptans or alcohols in the presence of an acid acceptor, e.g., sodium alkoxide. Sulfinyl and sulfonyl linked compounds can be prepared by oxidizing the appropriate sulfide linked compound with sodium metaperiodate or acidic hydrogen peroxide, respectively.

In most of the compounds prepared by Magee using the three above-described procedures, Y was hydrogen. Attempts to employ these procedures to synthesize compounds in which Y was a second X group using Method C produced only very small yields because of the number and variety of side reactions, and the oxime starting materials were not available for Methods A or B.

Another potential method of producing compounds where $R_5$ is a second X moiety, would seem to be the oximation of 2-keto-1,1-dithioacetals as illustrated by the equation:

$$\underset{R_3}{\overset{R_1}{\underset{|}{R_2-C}}}\overset{O}{\underset{\|}{-C}}-CHSR^2SR^3 + NH_2OH \longrightarrow$$

$$\underset{R_3}{\overset{R_1}{\underset{|}{R_2-C}}}\overset{NOH}{\underset{\|}{-C}}-CH(SR^2)(SR^3)$$

However, this method also has a limited success apparently because of the steric hinderance of the dithioacetal group as confirmed by P. E. Pearson and O. D. Keaton in a 1963 article in the *Journal of Organic Chemistry*, Volume 28, page 1557.

SUMMARY OF THE INVENTION

I have now discovered that compounds of the formula:

$$\underset{R_3}{\overset{R_1}{\underset{|}{R_2-C-C}}}\overset{O}{\underset{\|}{\overset{N-OCN}{\|}}}\overset{R_6}{\underset{R_7}{\diagdown}}\overset{H}{\underset{|}{C-X}}$$

where:

$R_1$ = hydrogen, $R_2$-$R_3$ or X;

$R_2$-$R_3$ = lower alkyl, lower alkenyl, lower alkynyl, substituted lower alkyl, alkenyl, or alkynyl with the proviso that $R_2$ and $R_3$ may be connected to form a cycloaliphatic ring;

$R_6$-$R_7$ = hydrogen, lower alkyl, lower alkenyl, or lower alkynyl;

Y = X or hydrogen;

X = is selected from the group consisting of $SR_8$, $S(O)R_8$, $SO_2R_8$, $OR_8$, $OSO_2R_8$, $NR_8R_9$, $NO_2$, CN, SCN, $N_3$, or halogen with the proviso that when X and Y are $OR_8$, $SR_8$, $S(O)R_8$, $SO_2R_8$, or $NR_8R_9$, X and Y may be connected to form a heterocyclic ring;

$R_8$ = hydrogen, lower alkyl, lower alkenyl, lower alkynyl, aryl, substituted aryl, carbamyl, substituted carbamyl, acyl, or substituted acyl with the proviso that the lower alkyl or alkenyl groups may be further substituted with X; and $R_9$ = hydrogen or lower alkyl with the proviso that $R_8$, $R_9$ and N in the $NR_8R_9$ group may form a heterocyclic ring.

wherein the term lower alkyl radical means a radical having from one to about seven carbon atoms can be prepared by the procedure illustrated in the following series of equations:

$$\underset{R_3}{\overset{R_1}{\underset{|}{R_2-C-CH}}}\overset{NOH}{\underset{\|}{}} \xrightarrow{Cl_2} \underset{R_3}{\overset{R_1}{\underset{|}{R_2-C-CCl}}}\overset{NOH}{\underset{\|}{}} \quad (1)$$

$$\underset{R_3}{\overset{R_1}{\underset{|}{R_2-C-CCl}}}\overset{NOH}{\underset{\|}{}} + \underset{Y}{\overset{H}{\underset{|}{LiCX}}} \longrightarrow \underset{R_3}{\overset{R_1}{\underset{|}{R_2-C-C}}}\overset{NOH}{\underset{\|}{-C}}\overset{H}{\underset{Y}{\underset{|}{-CX}}} \quad (2)$$

$$\underset{R_3}{\overset{R_1}{\underset{|}{R_2-C-C}}}\overset{NOH}{\underset{\|}{-C}}\overset{H}{\underset{Y}{\underset{|}{-C-X}}} + R_6N=C=O \longrightarrow \quad (3)$$

$$\underset{R_3}{\overset{R_1}{\underset{|}{R_2-C-C}}}\overset{NO-\overset{O}{\underset{\|}{C}}-NHR_6}{\underset{\|}{}}\overset{H}{\underset{Y}{\underset{|}{C-X}}}$$

The reaction of the first equation is disclosed in U.S. Pat. No. 3,658,869 to Soloway. It will, of course, also be obvious that the third step in the process of the present invention, the reaction with the isocyanate, substantially corresponds to Method A of U.S. Pat. No. 3,875,232.

DESCRIPTION OF THE PREFERRED EMBODIMENT

In the preferred embodiment, "X" is $S(O)_nR_8$ where n is 0, 1, or 2, and the process of the present invention is carried out at a temperature of from about $-96°$ C. to about $0°$ C. (preferably at about $-78°$ C.) in an inert solvent. As suitable inert solvents, mention may be made of methylene chloride, ethyl ether, tetrahydrofuran, dimethylsulfoxide and dimethylformamide. The process is preferably carried out at approximately atmospheric pressure, but can be conducted at pressures from as low as a slight vacuum, to as high as five atmospheres or more.

The following example will describe by way of illustration and not by way of limitation the novel process of the present invention.

EXAMPLE

Preparation of 3,3-Dimethyl-1-(methylsulfinyl)-1-(methylthio)-2-butanone Oxime

In a dry inert atmosphere, 12.7 ml of 1.58 M n-butyl lithium is added to a cooled ($-78°$ C.) solution of 2.48 g (0.020 mole) of methyl[methylsulfinyl)methyl]sulfide in 30 ml of methylene chloride. A white precipitate was formed toward the end of the addition. While maintaining the low temperature, 1.35 g (0.010 mole) of N- hydroxy-2,2-dimethylpropanimidoyl chloride in 5 ml of methylene chloride was added in one portion. The solution was stirred at −78° C. for 30 min. and then allowed to come to room temperature.

After two hours, the solution was poured into a stirring saturated ammonium chloride solution. The organic layer was removed and washed with two small portions of water. After drying ($Na_2SO_4$) and concentrating the organic phase, 2.53 g of a pale yellow oil was obtained. A total of 0.500 g (22%) of 3,3-dimethyl-1-(methylsulfinyl)-1-(methylthio)-2-butanone oxime was isolated by dry column chromatography of 2.3 g of the crude oil.

Diastereomer A: nmr δ ($CDCl_3$): 1.25 ppm (9H, s, t-Butyl); 2.28 (3H, s, $SCH_3$); 2.81 (3H, s, $SOCH_3$); 4.0 (1H, s, methine); 10.4 (1H, broad, OH).

Diastereomer B: nmr δ ($CDCl_3$): 1.25 ppm (9H, s, t-Butyl); 2.38 (3H, s, $SCH_3$); 2.53 (3H, s, $SOCH_3$); 3.85 (1H, s, methine); 10.4 (1H, broad, OH).

Diastereomeric Mixture

IR $\lambda_{max}$ (Neat): 3150 cm$^{-1}$, hydrogen bonded OH; 2900 and 2800 cm$^{-1}$, C—H stretching; 1620 cm$^{-1}$, C=N, 1450; 1400; 1355; 1320; 1280; 1240; 1205; 1080; 1010; S=O; 960; 875; 790; and 768 cm$^{-1}$.

Preparation of (Z)-3,3-Dimethyl-1-(Methylsulfinyl)-1 Methylthio-Butanone-(N-Methylcarbamoyl)oxime To 50 mg of 3,3-dimethyl-1-(methylsulfinyl)-1-methylthio-2-butanone oxime in 5 ml of methylene chloride is added 0.5 ml of methyl isocyanate. After standing at room temperature 18 hrs., the solvent was removed to give 53 mg of impure 3,3-dimethyl-1-(methylsulfinyl)-1-methyl-thio-2-butanone O-[methylaminocarbonyl]oxime. The ir and nmr were identical to that of an authentic sample synthesized independently.

Diastereomer A: nmr δ ($CDCl_3$): 1.30 ppm (9H, s, t-Butyl); 2.35 (3H, s $SCH_3$); 2.88 (3H, s, $SOCH_3$); 2.88 (3H, d, J=4 hz, N-$CH_3$); 4.09 (1H, s, methine); 6.13 (1H, broad, NH).

Diastereomer B: nmr δ ($CDCl_3$): 1.30 ppm (9H, s, t-Butyl); 2.41 (3H, s, $SCH_3$); 2.55 (3H, s, $SOCH_3$); 2.88 (3H, d, J=4 hz, N-$CH_3$); 3.92 (1H, s, methine); 6.13 (1H, broad, NH).

Diastereomeric Mixture

IR $\lambda_{max}$ (Neat): 3360 cm$^{-1}$ (m, b, N-H); 2960 (m, CH stretch); 1730 (s, CO stretch); 1620 (w, C=N stretch); 1510, 1500 and 1475 (s); 1410 (m); 1365 (m); 1225, and 1220 (s); 1110 (m); 1070 (m); 1040 (s, S=O stretch); 980 (w); 940 (m); 895 (m).

While the process of the present invention has particular applicability to the synthesis of compounds wherein Y is X, the process has applicability to all of the compounds disclosed in U.S. Pat. No. 3,875,232 and particular applicability to the synthesis of those compounds where X is S(Q)$_n$R where n=0, 1, or 2.

It will be apparent to those skilled in the art that many alterations and changes may be made in the materials, compounds, and procedures hereinbefore without departing from the topic of the present invention, and it is my intention it be limited by the appended claims.

What is claimed is:

1. A method of preparing ketoximes of the formula:

where:
$R_1$=hydrogen, $R_2$-$R_3$ or X;
$R_2$-$R_3$=lower alkyl, lower alkenyl, lower alkynyl with the proviso that $R_2$ and $R_3$ may be connected to form a cycloaliphatic ring;
Y=H or X;
X=is selected from the group consisting of $SR_8$, $S(O)R_8$, or $SO_2R_8$, and
$R_8$=hydrogen, lower alkyl, lower alkenyl, lower alkynyl, or aryl;
which comprises halogenating an oxime of the formula:

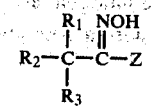 (1)

to form a halogenated intermediate of the formula:

wherein Z is an active halogen; and reacting said halogenated intermediate with a compound of the formula:

$$A-\underset{\underset{Y}{|}}{\overset{\overset{X}{|}}{C}}-H$$

wherein A is a member selected from the group consisting of Li, Na, and K.

2. The process according to claim 1 wherein said reaction is carried out in an inert solvent at a temperature of from about −96° C. to about 0° C. and at a pressure of not more than about five atmospheres.

3. The process according to claim 2 wherein said solvent is a member selected from the group consisting of methylene chloride, diethyl ether, tetrahydrofuran, dimethylsulfoxide and dimethylformamide.

4. The process according to claim 2 wherein A is lithium and Z is chlorine.

5. A method of preparing ketoxime carbamates of the formula:

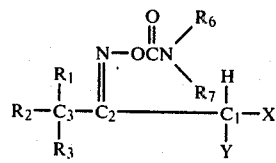

where:
$R_1$=hydrogen, $R_2$-$R_3$ or X;
$R_2$-$R_3$=lower alkyl, lower alkenyl, lower alkynyl, with the proviso that $R_2$ and $R_3$ may be connected to form a cycloaliphatic ring;

$R_6$–$R_7$ = hydrogen, lower alkyl; lower alkenyl, or lower alkynyl;

Y = H or X;

X = is selected from the group consisting of $SR_8$, $S(O)R_8$, or $SO_2R_8$, and $R_8$ = hydrogen, lower alkyl, lower alkenyl, lower alkynyl, or aryl, which comprises halogenating an oxime of the formula:

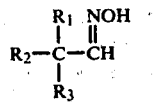 (1)

to form a halogenated intermediate of the formula:

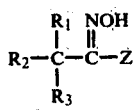

wherein Z is an active halogen; and reacting said halogenated intermediate with a compound of the formula:

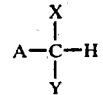

wherein A is a member selected from the group consisting of Li, Na, and K; to form a Ketoxime of the formula:

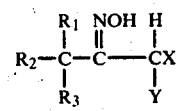

reacting said ketoxime with an isocyanate of the formula $R_6NCO$ to form said ketoxime carbamate.

6. The process according to claim 5 wherein said reaction to form said ketoxime is carried out in an inert solvent at a temperature of from about −96° C. to about 0° C. and at a pressure of not more than five atmospheres.

7. The process according to claim 6 wherein said solvent is a member selected from the group consisting of methylene chloride, ethyl ether, tetrahydrofuran, dimethylsulfoxide and dimethylformamide.

8. The process according to claim 6 wherein A is lithium and Z is chlorine.

* * * * *